(12) United States Patent
Schneiter

(10) Patent No.: US 7,691,107 B2
(45) Date of Patent: Apr. 6, 2010

(54) RONGEUR

(76) Inventor: James A. Schneiter, 200 Dover Cir., Lake Forest, IL (US) 60045

( * ) Notice: Subject to any disclaimer, the term of this patent is extended or adjusted under 35 U.S.C. 154(b) by 262 days.

(21) Appl. No.: 11/529,696

(22) Filed: Sep. 26, 2006

(65) Prior Publication Data

US 2007/0093843 A1    Apr. 26, 2007

Related U.S. Application Data

(60) Provisional application No. 60/722,484, filed on Sep. 30, 2005.

(51) Int. Cl.
*A61B 17/00*    (2006.01)
(52) U.S. Cl. ........................................................ 606/83
(58) Field of Classification Search .................. 606/83, 606/82, 84, 85
See application file for complete search history.

(56) References Cited

U.S. PATENT DOCUMENTS

| 5,451,227 | A | 9/1995 | Michaelson |
| 5,702,420 | A * | 12/1997 | Sterling et al. ............... 606/205 |
| 5,961,531 | A | 10/1999 | Weber et al. |
| 6,126,674 | A | 10/2000 | Janzen |
| 6,621,294 | B2 * | 9/2003 | Hsu et al. ...................... 326/37 |
| 6,638,280 | B2 * | 10/2003 | Agbodoe ...................... 606/83 |
| 6,685,710 | B2 | 2/2004 | Agbodoe |
| 6,723,103 | B2 | 4/2004 | Edwards |
| 6,991,633 | B2 | 1/2006 | Agbodoe |
| 7,011,663 | B2 | 3/2006 | Michelson |
| 2006/0114094 | A1 * | 6/2006 | Jean et al. .................... 336/182 |
| 2006/0224160 | A1 * | 10/2006 | Trieu et al. .................... 606/83 |

* cited by examiner

*Primary Examiner*—Eduardo C Robert
*Assistant Examiner*—Elana B Fisher
(74) *Attorney, Agent, or Firm*—Brinks Hofer Gilson & Lione

(57) ABSTRACT

A rongeur having a fixed shank and a moveable crossbar is disclosed. The crossbar is connected to and axially aligned with the fixed shank. The crossbar has a distal end with a cutting portion located therein. A port is connected to one of the fixed shank and the moveable crossbar. An access channel is connected to the port for improved flushing, cleaning, sterilization, drying and lubricating capabilities in a rongeur.

20 Claims, 5 Drawing Sheets

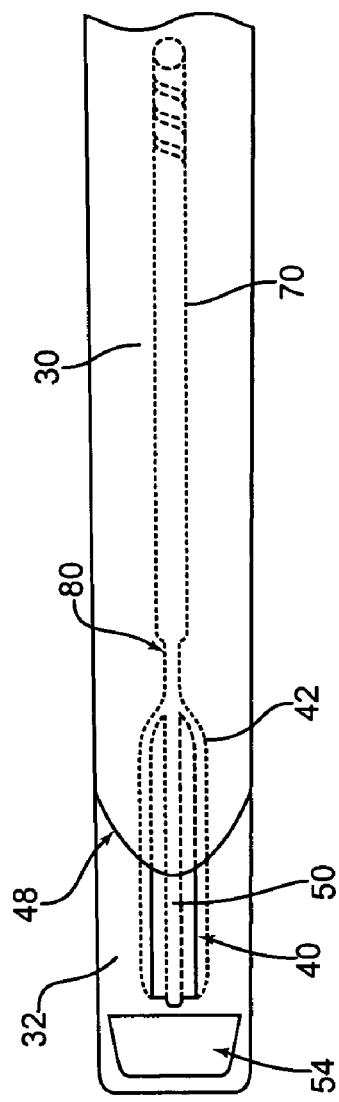
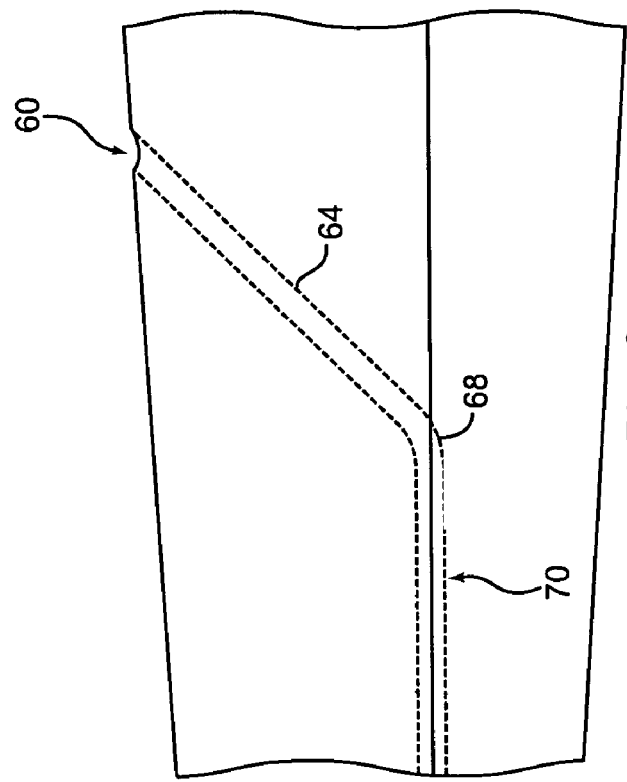

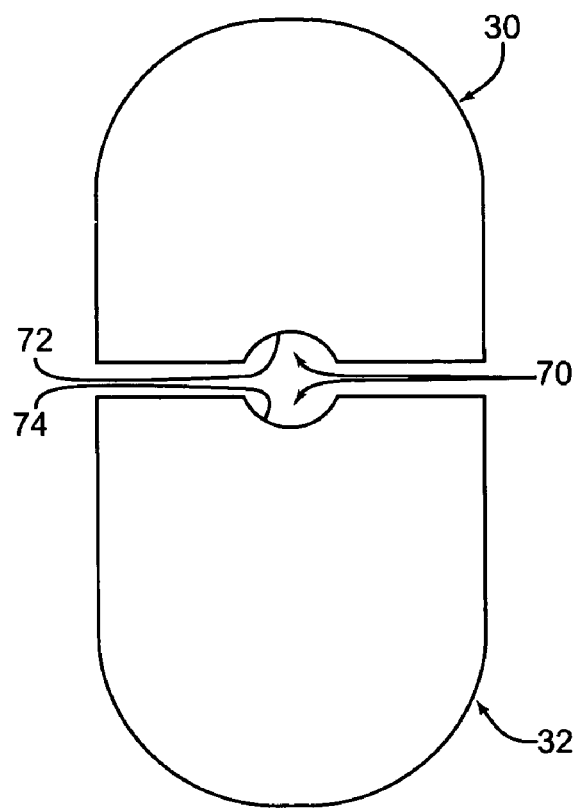
Fig.4
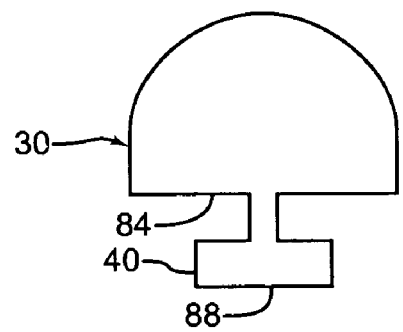
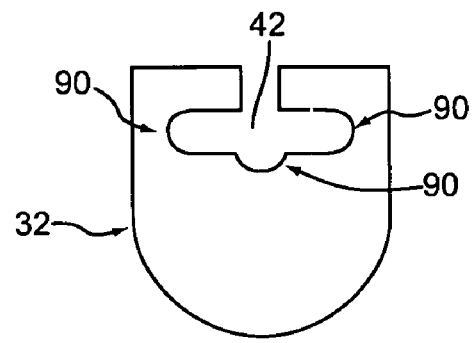
Fig.5 ns and make the sterilization process ineffective.
RONGEUR

RELATED APPLICATIONS

This patent application claims priority and the benefit under 35 U.S.C. §119(e) to U.S. Provisional Patent Application No. 60/722,484, filed Sep. 30, 2005, which is hereby incorporated by reference.

FIELD OF THE INVENTION

The present invention relates generally to the field of medical instruments. More specifically, the present invention relates to a rongeur having improved flushing, cleaning, sterilization, drying and lubricating capabilities.

BACKGROUND

A rongeur is a hand held surgical instrument used to remove a small amount of body material for testing. A rongeur can be utilized to remove cartilage or other types of biomass and/or tissue from the knee, cervix, or vertebrae in a patient's back or other sites within the body. During the normal operation of a rongeur, blood, mucous, tissue, bone and other bio-burden can infiltrate and become trapped within the instrument. A rongeur includes interfacing surfaces and a cutting surface that can trap bio-burden during normal use and which may not be completely removed during the cleaning process. Entrapped bio-burden can inhibit the sterilization process and the sterility of the instrument after re-processing cannot be guaranteed. Also, unless the instrument is thoroughly dried after the sterilization cycle, waterborne pathogens can survive in inaccessible spaces and further result in a contaminated instrument. Use of a contaminated instrument creates an increased risk of a surgical infection to the patient.

Inadequate or improper cleaning and sterilization of surgical instruments has been documented by the Center for Disease Control (CDC) to be a major cause of surgical site infections (SSI's). A recent CDC publication, "Guideline for Prevention of Surgical Site Infection," pointed out that SSI's are particularly troublesome because "one third involved organs and spaces accessed during the operation. When surgical patients with SSI's died, 77 percent of the deaths were reported to be related to the infection and the majority, 93 percent, were serious infections involving organs and spaces accessed during the operation."

According to recent data collected by the CDC, the distribution of pathogens isolated from SSI's has remained stubbornly consistent over the last decade. This fact is especially disturbing in light of their observation that, "[a]dvances in infection control practices include improved operating room ventilation, sterilization methods and barriers, surgical techniques and availability of antimicrobial prophylaxis. Despite these activities, SSI's remain a substantial cause of morbidity and mortality among hospitalized patients." Reusable surgical instruments (such as rongeurs) that are not, or cannot be, properly cleaned and sterilized are a major cause of these deep organ SSI's. The CDC further notes that "[i]nadequate cleaning and sterilization of surgical instruments has resulted in SSI outbreaks" and cites articles in Anesthesiology, MMWR and Journal of Hospital Infections in asserting this claim.

The April 2001 AORN Journal (Association of periOperative Registered Nurses) noted, "[d]econtamination is the first and most important step in the sterilization process. Inadequate cleaning of organic debris may result in retained organisms and make the sterilization process ineffective. Proper decontamination and removal of all possible biomaterial is essential. High bio-burden inhibits the sterilization process, and sterility cannot be guaranteed. If an improperly cleaned instrument is placed on the sterile field in the operating room, the sterile field should be considered contaminated, and appropriate steps to correct the problem should be taken. The un-sterile instrument and other instruments that may have come in contact with it should be removed from the operating room."

New research in The Journal of the American Medical Association (JAMA) released Oct. 7, 2003 concluded, "[m]edical injuries in hospitals pose a significant threat to patients and incur substantial costs to society." Hospital acquired infections (HAI's) top the list of medical injuries in both costs and additional days of hospitalization required. The largest risk to patients are infections acquired during surgery which "result in almost eleven additional days of hospital care at an extra cost of $57,727 as well as an increased risk of death of twenty two percent." In April 2002, an article in Infection Control Today stated, "[o]ne concern that is getting more attention is the development of biofilms (a layer of microorganisms that contain a polysaccharide matrix) on instruments/medical devices or within instruments that cannot be taken apart or contain multiple complex contours (i.e., rasps, reamers, rongeurs, broaches or complex endoscopic instruments). The incorporation of pathogens in biofilms can protect the pathogen from concentrations of biocides that could otherwise kill or inhibit those organisms freely suspended in water. Biofilms provide a safe haven for organisms, thus creating the potential of cross contamination/infection."

Once protected within a biofilm, bacteria are able to resist antibiotics at concentrations ranging from 1 to 1.5 thousand times higher than the concentrations used in conventional antibiotic therapy. As a consequence, biofilms are a source of serious and chronic infections. With the increasing emergence of antibiotic-resistant bacteria, biofilm-related chronic infections transmitted by non-sterile surgical instruments represent a highly complex and escalating medical problem.

The risk of a surgical infection caused by waterborne pathogens remaining inside a surgical instrument after the sterilization cycle has also been receiving increased attention. "The most common misconception in healthcare settings is that waterborne pathogens are not major contributors to infections," says Joseph S. Cervia, Md., professor of Clinical Medicine at the Albert Einstein College of Medicine in New York (Infection Control Today, June 2005). Dr. Cervia goes on to point out, "modes of transmission for waterborne infections include contact from an improperly reprocessed medical device."

In attempting to solve the problem of bio-burden and/or waterborne pathogens collecting on the internal interfacing surfaces of rongeurs, a number of techniques and rongeurs have been developed. Several styles of rongeurs have been developed that can be taken apart to expose all surfaces to the cleaning process. This approach can be effective if done properly by a skilled and knowledgeable re-processing technician. The down-side to taking apart rongeurs is that they can be difficult and time consuming to disassemble, manually clean and reassemble, not to mention the frequent problem of lost parts. If not properly reassembled, the rongeur will not operate properly and may require costly repair or replacement. Once reassembled and sterilized, the rongeur can still pose the risk of a surgical site infection ("SSI") to a patient due to waterborne pathogens remaining inside the instrument in areas that cannot be properly dried after the sterilization cycle. While other approaches have been suggested involving the use of more complicated instruments, these approaches create new levels of manufacturing and user complexity.

Another problem associated with rongeurs is the inability to properly lubricate all of the contact surfaces without completely disassembling the instrument. This time consuming process is expensive and is frequently done by a professional instrument repair service requiring the instrument to be taken out of service. Lack of proper lubrication makes the instrument difficult, if not impossible, to use. Lack of proper lubrication inside the instrument causes galling of the metal and significantly shortens the life of the instrument.

Accordingly, there exists a need for a rongeur that improves and simplifies the cleaning, sterilization, drying and lubricating processes while still providing easy use thereof.

SUMMARY OF THE INVENTION

The present invention is directed to a rongeur with improved flushing, cleaning, sterilization, drying and lubricating capabilities.

According to a first aspect of the invention, a rongeur having a fixed shank and a moveable crossbar is provided. The crossbar is connected to and axially aligned with the fixed shank. The crossbar has a distal end with a cutting portion located therein. A port is connected to one of the fixed shank and the moveable crossbar. An access channel is connected to the port.

According to another aspect of the invention, a rongeur having a fixed shank and moveable crossbar is provided. The fixed shank has a distal end with a footplate located therein and a first interfacing surface. A moveable crossbar is connected to and axially aligned with the fixed shank and includes a second interfacing surface. The crossbar has a distal end with a cutting portion located therein. A port is connected to one of the fixed shank and the moveable crossbar. An access channel is connected to the port and extends axially along and between the fixed shank and the moveable crossbar. The port and the access channel provide for improved flushing of the first and second interfacing surfaces.

According to a further aspect of the invention, a rongeur having a fixed shank and a crossbar is provided. The fixed shank has a distal end with a footplate located therein and a first interfacing surface that is micro-polished. The moveable crossbar is connected to and axially aligned with the fixed shank. The crossbar has a distal end with a cutting portion located therein and a second interfacing surface resting against the first the interfacing surface. The second interfacing surface is micro-polished. A port is connected to one of the fixed shank and the moveable crossbar. An access channel is connected to the port and extends axially along and between the fixed shank and the moveable crossbar whereby the port and the access channel provides for improved flushing of the first and second interfacing surfaces.

The present invention, together with attendant objects and advantages, will be best understood with reference to the detailed description below in connection with the attached drawings.

BRIEF DESCRIPTION OF THE DRAWINGS

FIG. 2 is a top view of the distal end of the rongeur with the crossbar in the cutting position.

FIG. 3 is a side view of the rongeur with the port and access channel illustrated in dashed lines.

FIG. 4 is a cross-section of the rongeur along the lines 4-4 (as shown in FIG. 1) illustrating an embodiment of the access channel.

FIG. 5 is a cross-section of the rongeur along the lines 5-5 (as shown in FIG. 1) illustrating the retaining rail and receiving channel.

DETAILED DESCRIPTION OF THE DRAWINGS AND THE PRESENTLY PREFERRED EMBODIMENTS

The present invention is directed to an improved medical instrument such as a rongeur that is more readily flushed, cleaned, sterilized, dried and lubricated than those commonly used. While the present invention is directed generally to rongeurs, it applies to many specific types of rongeurs such as Kerrison, Lempert, Schlesinger, Cushing, Stille-Horsley or Sella Punch Rongeurs. The present invention is directed to rongeurs having a variety of sizes and shapes as know in the art. In particular, the present invention is useful with rongeurs having a variety of different cutting surfaces, sizes and shapes as well as different sizes, configurations and shapes for the handles and fixed shanks. The present invention also applies to other types of medical instruments that have inaccessible surfaces that are difficult, if not impossible, to properly flush, clean, sterilize, dry or lubricate.

As used herein, the term "body material" should be interpreted broadly to include any specimen of material such as bone, cartilage, blood, or other types of bio-burden. The term "access channel" should also be interpreted broadly to include any passageway in the instrument, regardless of size or shape, that is operative to perform the cleaning, flushing, sterilization, drying or lubricating of the instrument.

Figure 1:
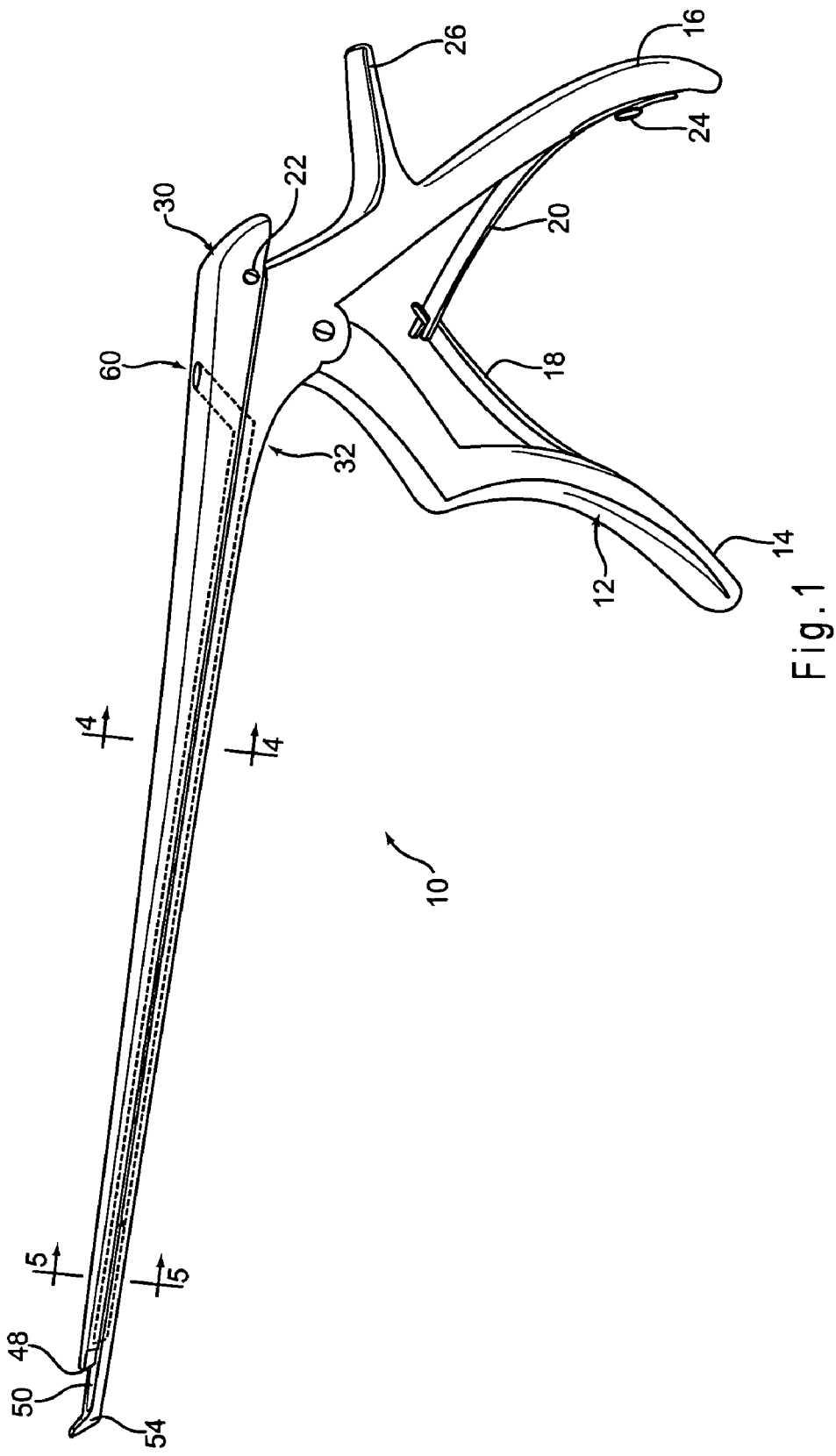
FIG. 1 is a perspective view of rongeur according to an embodiment of the present invention with the crossbar illustrated in the open or cutting position.

FIG. 1 is an illustration of a rongeur 10, according to an embodiment of the present invention shown in the open or cutting position. The rongeur 10 includes a handle 12 having a front grip 14 and a rear grip 16. Spring elements 18, 20 force apart the front grip 14 and the rear grip 16. The front grip 14 and rear grip 16 are pivotably interconnected by means of the screw 22. Two additional screws (one shown) 24 are used to secure the spring elements 18, 20 to the front grip 14 and the rear grip 16. The rear grip 16 includes a thumb portion 26 that accommodates the thumb of a surgeon. The crossbar 30 is slideably positioned over the fixed shank 32. The crossbar 30 moves in a reciprocating plane that is axially aligned with respect to the fixed shank 32. The crossbar 30 is slidably connected to the fixed shank by means of a rail 40 and a receiving channel 42 (best illustrated in FIG. 5). FIG. 5 is a cross-section of the rongeur along the lines 5-5 (as shown in FIG. 1). As shown in FIG. 5, the rail 40 projects downward from the crossbar 30 and is slideably received within the channel 42. In the present embodiment, the receiving channel 42 forms a portion of the access channel that is described herein. Materials such as stainless steel and tungsten carbide are commonly used to form the rongeur 10. Those materials may further be micro-polished to decrease the ability of bio-burden to adhere to the surface of the instrument, increase the effectiveness of the detergent flush to remove bio-burden, increase bacterial kill rates during the sterilization cycle, increase the volume of moisture removed during the drying cycle, increase the effectiveness of the lubrication process, improve the overall function and operation of the instrument, and extend the useful life of the instrument.

Referring back to FIG. 1, the front grip 14 is connected to crossbar 30 such that when it is squeezed, the crossbar 30 is driven forward. With further reference to FIG. 2, the crossbar 30 includes a distal ending having a cutting surface 48 adjacent a bite opening 50. A footplate 54 is located at the distal end of the fixed shank 32. As illustrated in FIGS. 1-2, the spring elements 18, 22 hold the cutting surface 48 in the open position or spaced apart from the footplate 54. The cutting surface 48 and footplate 54 can include a recess that retains the severed material.

During an operation, the surgeon squeezes or compresses the front grip 14 when the bite opening 50 is adjacent the desired body material. By squeezing the front grip 14 toward the rear grip 16, the cutting surface 48 is drawn toward the footplate 54. When the cutting surface 48 contacts the tissue, it "bites" the body material or tissue to remove a specimen for testing. When the surgeon releases the pressure on the front grip 14 and the rear grip 16, the spring elements 18, 20 force the front grip 14 and rear grip 16 apart thereby sliding the crossbar 30 and particularly cutting surface 48 away from the footplate 54. This is the open position illustrated in FIG. 1 and the position from which the specimen can be removed.

One embodiment of the port 60 and access channel 42 is illustrated in FIGS. 1-5. With reference to FIG. 3, the port 60 is located in the crossbar 30. In the illustrated embodiment, the port 60 has a diameter of 0.080". The access channel 42 has an angled throat portion 64. The throat portion 64 has a diameter that tapers down to 0.050" at the proximal end 68. The taper of the throat portion 64 provides for a compression fit between the wall of the throat and an infusion cannula that is inserted into the port 60 for distributing the flushing solution into access channel 42. The taper of the throat portion 64 also increases the velocity of the cleaning solution to thereby provide a more effective cleaning. With reference to FIG. 4, a cross-section of the axial portion 70 of the access channel 42 is illustrated. FIG. 4 is a cross-section of the rongeur along the lines 4-4 (as shown in FIG. 1) illustrating an embodiment of the access channel. The axial portion 70 includes a curved upper portion 72 in the crossbar 30 and a curved lower portion 74 in the fixed shank 32. With reference to FIG. 2, the axial portion 70 has a narrowed throat portion 80 at the distal end. The throat portion 80 has a reduced diameter 0.040" that serves to increase the venturi effect of any cleaning solution passing therethrough.

Adjacent the throat portion 80, the rail 40 projects downward from the crossbar 30 into the receiving channel 42. With reference to FIG. 5, the rail 40 has an I-beam shape with cutout portions 84 and a bottom surface 88. The receiving channel 42 has an inverted cross-like shape that is sized to accommodate the rail 40. The receiving channel 42 has curved, cornerless portions 90 that allow for the cleaning solution to pass along the surfaces of the rail 40 to remove trapped bio-burden, permit the steam to reach these surfaces during the sterilization cycle to increase bacterial kill rates, void residual moisture from these surfaces during the drying cycle to decrease the risk of waterborne pathogens contaminating the instrument, and to permit proper lubrication of the instrument.

Conventional cleaning solutions such as enzymatic detergents or any other approved medical device cleaning solution may be used. The cleaning solutions are inserted through the port 60 into the access channel 70 using a cannula attached to an infusion device such as a syringe in order to flush and clean the rongeur 10. In particular, the crossbar 30 and fixed shank 32 are exposed to body material such as tissues or fluids that can collect within the space between the crossbar 30 and the fixed shank 32. In contrast to previous rongeurs, the access channel 70 provides a means for cleaning the space between the interfacing surfaces of the crossbar 30 and the fixed shank 32 and the area around the rail 40. The access channel 70 serves as a conduit for the steam to penetrate the interior of the instrument during the sterilization cycle to increase bacteria kill and reduce the risk of a contaminated instrument infecting a patient.

In an alternate embodiment, the access channel 70 may be used for improved drying of the rongeur 10. During the sterilization process, moisture collects in the internal recesses of the instrument. This residual moisture can contain waterborne pathogens that result in a contaminated instrument after the sterilization cycle. The access channel 70 provides a means to void the instrument of residual moisture during the drying cycle and minimize the risk of waterborne pathogens remaining inside the instrument.

In another alternate embodiment, conventional lubrication solutions or materials may be used to properly lubricate the rongeur 10. The lubricant is inserted through the port 60 into the access channel 70 using a cannula attached to an infusion device such as a syringe in order to lubricate the internal surfaces of the rongeur 10. The access channel 70 provides a means for lubricating the space between the interfacing surfaces of the crossbar 30 and the fixed shank 32 and the area around the rail 40. The access channel 70 provides a conduit to infuse an instrument lubricant into the instrument to reduce galling, improve instrument performance and extend the useful life of the instrument without having to go through the time consuming, expensive process of disassembling, lubricating and then reassembling the instrument.

Figure 6:
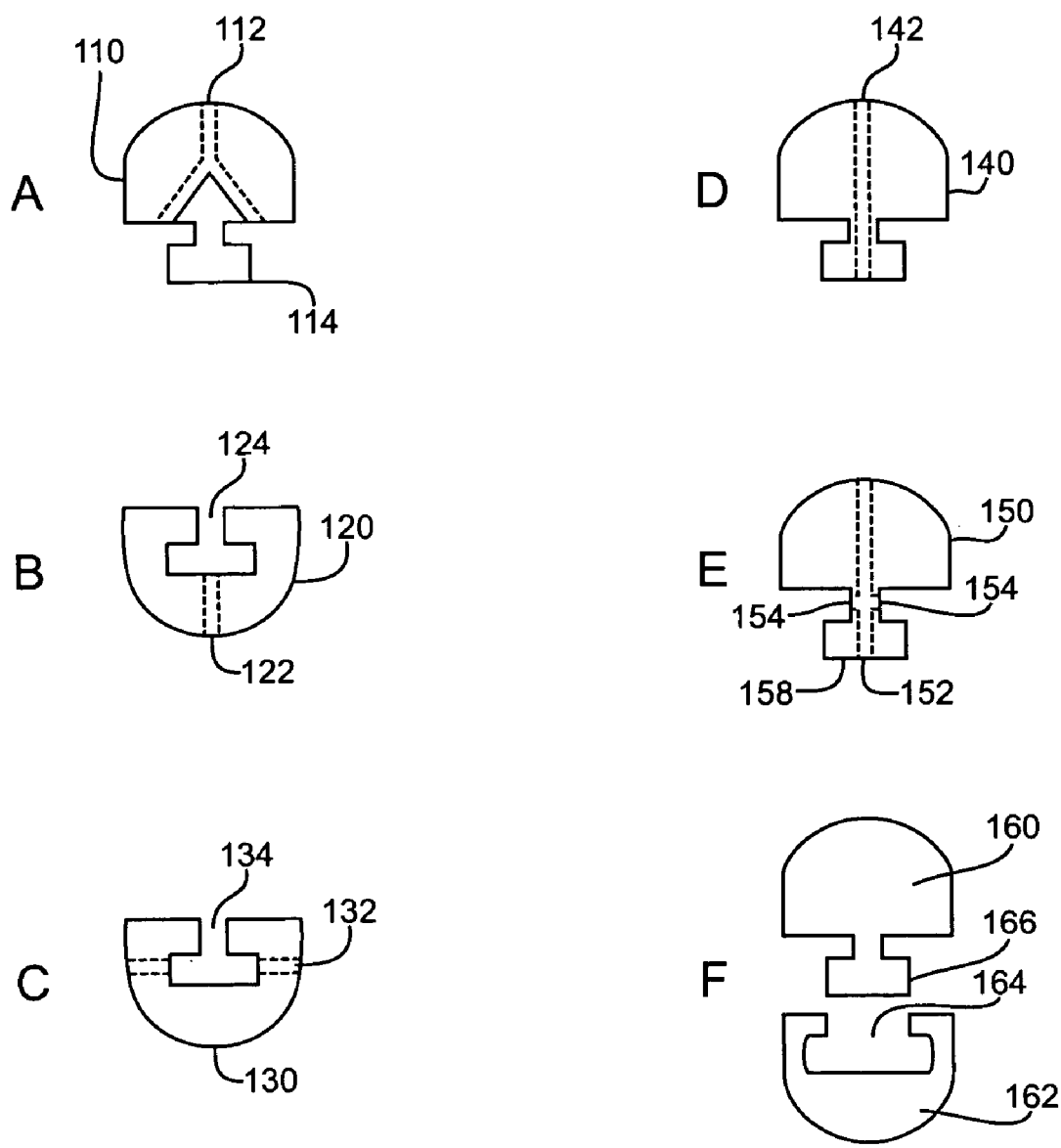
FIGS. 6A-6F illustrates additional embodiments of the access channel passing through at least one of the crossbar and fixed shank.

FIG. 6 illustrates six additional embodiments of the present invention. The crossbar 110, of FIG. 6A, illustrates an access channel 112 having an inverted Y-shaped configuration adjacent the rail 114. FIG. 6B illustrates an embodiment of the fixed shank 120 having an access channel 122 extending downward from the receiving channel 124. FIG. 6C illustrates an embodiment of the fixed shank 130, similar to the embodiment of FIG. 6B, except that the access channel 132 extends outward from the receiving channel 134. FIGS. 6D & 6E illustrate two additional crossbar embodiments 140, 150. The crossbar 140 of FIG. 6D includes an access channel 142 that extends downward through the center thereof. The crossbar 150, of FIG. 6E, includes a similar access channel 152 with two additional side openings 154 extending through a portion of the rail 158. The crossbar 160 and fixed shank 162 illustrated in FIG. 6F include an alternate form of the receiving channel 164 that receives the rail 166. These embodiments may optionally include a port 60 and an access channel 70 as illustrated in FIGS. 1-5.

Figure 7:
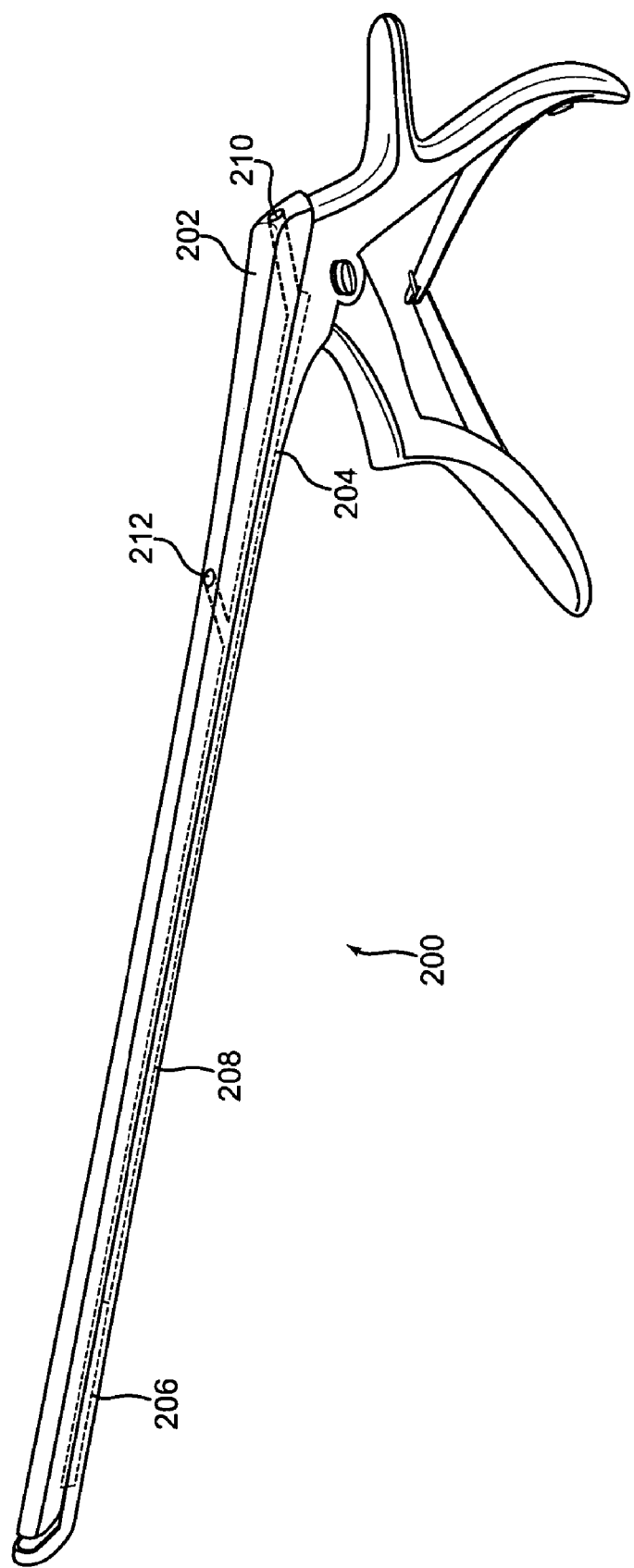
FIG. 7 illustrates another embodiment of a rongeur according to the present invention.

FIG. 7 illustrates another embodiment of a rongeur 200 that is substantially similar to the embodiment of FIGS. 1-5 except that the crossbar 202 includes two spaced apart rail portions 204, 206 that are received by the receiving channel 208. The rongeur 200 also includes two ports 210, 212 to provide fluid access to the receiving channel.

The embodiments described above and shown herein are illustrative and not restrictive. The scope of the invention is indicated by the claims rather than by the foregoing description and attached drawings. The invention may be embodied in other specific forms without departing from the spirit of the invention. For example, the size, number and shape of the primary ports and access channels may be designed in a manner other than as specifically described or illustrated in the figures. Accordingly, these and any other changes which come within the scope of the claims are intended to be embraced herein.

I claim:

1. A rongeur comprising,
   a) a fixed shank having a first interfacing surface and a distal end comprising a footplate;
   b) a moveable crossbar that is connected to and axially aligned with the fixed shank, the movable crossbar having a distal end with a cutting portion located therein and a second interfacing surface configured for mating with the first interfacing surface;
   c) a port connected to one of the fixed shank and the moveable crossbar, the port located in a proximal end of one of the fixed shank and the movable crossbar; and
   d) an access channel connected to the port and configured for providing fluid access to an interior of the rongeur, the access channel extending axially and longitudinally through the first and second interfacing surfaces between the fixed shank and the movable crossbar and opening adjacent the cutting portion of the crossbar.

2. The rongeur of claim 1 wherein the access channel includes an upper portion and a lower portion, the lower portion having a channel adapted to receive a rail projecting from the crossbar.

3. The rongeur of claim 2 wherein the lower portion has an inverted rounded cross-like shape.

4. The rongeur of claim 2 wherein the access channel is located in the shank.

5. The rongeur of claim 2 wherein the port and the access channel are located in the crossbar.

6. The rongeur of claim 2 wherein the port is located in the crossbar and the access channel passes within both the crossbar and the shank.

7. The rongeur of claim 6 wherein the access channel includes two curved portions, a top curved portion passing axially along the crossbar and a bottom curved portion passing axially along the shank.

8. The rongeur of claim 2 wherein the access channel includes more than one fluid flow path.

9. The rongeur of claim 2 wherein the access channel is micro-polished.

10. A rongeur comprising,
    a) a fixed shank having a first interfacing surface and a distal end comprising a footplate;
    b) a moveable crossbar that is connected to and axially aligned with the fixed shank, the movable crossbar having a distal end with a cutting portion located therein and a second interfacing surface configured for mating with the first interfacing surface;
    c) a port connected to one of the fixed shank and the moveable crossbar, the port located in a proximal end of one of the fixed shank and the movable crossbar; and
    d) an access channel connected to the port and configured for providing fluid access to an interior of the rongeur, the access channel extending axially and longitudinally through the first and second interfacing surfaces between the fixed shank and the movable crossbar and opening adjacent the cutting portion of the crossbar whereby the port and the access channel provide for improved flushing of the first and second interfacing surfaces.

11. The rongeur of claim 10 wherein the access channel includes an upper portion and a lower portion, the lower portion having a channel adapted to receive a rail projecting from the crossbar.

12. The rongeur of claim 11 wherein the lower portion has an inverted rounded cross-like shape.

13. The rongeur of claim 12 wherein the access channel includes more than one fluid flow path.

14. The rongeur of claim 11 wherein the port and the access channel are located in the crossbar.

15. The rongeur of claim 14 wherein the access channel includes two curved portions, a top curved portion passing axially along the crossbar and a bottom curved portion passing axially along the shank.

16. A rongeur comprising,
    a) a fixed shank having a first interfacing surface that is micro-polished and a distal end comprising a footplate;
    b) a moveable crossbar that is connected to and axially aligned with the fixed shank, the movable crossbar having a distal end with a cutting portion located therein and a second interfacing surface configured for mating with the first interfacing surface, the second interfacing surface being micro-polished;
    c) a port connected to one of the fixed shank and the moveable crossbar, the port located in a proximal end of one of the fixed shank and the movable crossbar; and
    d) an access channel connected to the port and configured for providing fluid access to an interior of the rongeur, the access channel extending axially and longitudinally through the first and second interfacing surfaces between the fixed shank and the movable crossbar and opening adjacent the cutting portion of the crossbar whereby the port and the access channel provide for at least one of improved flushing, cleaning, sterilizing and lubricating of the first and second interfacing surfaces.

17. The rongeur of claim 16 wherein the access channel is micro-polished.

18. The rongeur of claim 17 wherein the port and the access channel are located in the crossbar.

19. The rongeur of claim 18 wherein the access channel includes two curved portions, a top curved portion passing axially along the crossbar and a bottom curved portion passing axially along the shank.

20. The rongeur of claim 19 wherein the access channel includes more than one fluid flow path.

* * * * *